United States Patent [19]

Meyer

[11] 3,957,886
[45] May 18, 1976

[54] PROCESS FOR THE PURIFICATION OF 2,2-BIS-(4-HYDROXY-3,5-DICHLOROPHENYL)-PROPANE

[75] Inventor: Karl-Heinrich Meyer, Krefeld-Bockum, Germany

[73] Assignee: Bayer Aktiengesellschaft, Leverkusen, Germany

[22] Filed: Nov. 14, 1973

[21] Appl. No.: 415,830

[30] Foreign Application Priority Data
Nov. 14, 1972 Germany............................ 2255638

[52] U.S. Cl................................. 260/619 R; 260/619 A
[51] Int. Cl.$^2$................... C07C 37/44; C07C 39/16
[58] Field of Search................... 260/619 R, 619 A

[56] References Cited
UNITED STATES PATENTS
3,850,994   11/1974   Zoche et al..................... 260/619 R FOREIGN PATENTS OR APPLICATIONS
1,237,335   10/1969   United Kingdom............. 260/619 R

*Primary Examiner*—Norman Morgenstern
*Attorney, Agent, or Firm*—Plumley & Tyner

[57] ABSTRACT

A process for the production of very pure 2,2-bis-(4-hydroxy-3,5-dichlorophenyl)-propane (TCB), wherein a solution of TCB in an aromatic hydrocarbon is treated with hot water, followed by crystallization of TCB from the aqueous solution by addition of a halogenated aliphatic hydrocarbon.

6 Claims, No Drawings

PROCESS FOR THE PURIFICATION OF 2,2-BIS-(4-HYDROXY-3,5-DICHLOROPHENYL)-PROPANE

It is known that bisphenols, for example, 2,2-bis-(4-hydroxyphenyl)-propane, can be chlorinated in solution or suspension in inert hydrocarbons as solvents by the introduction of gaseous chlorine. After the solvent has been distilled off and the excess chlorine removed, a chlorinated bisphenol is obtained, which unfortunately cannot be used for a number of applications. For example, this crude product is not suitable for the production of high molecular, substantially non-inflammable polycondensation products because, in addition to nuclear-chlorinated cleavage products, it also contains compounds with chlorinated aliphatic side chains. These compounds eliminate HCl during the thermoplastic processing of plastics and are therefore troublesome.

Accordingly, attempts have been made to improve the quality of the chlorinated bisphenol (TCB) = 2,2-bis-(4-hydroxy-3,5-dichlorophenyl)-propane by subjecting it to various purification processes. However, even repeated, complicated recrystallization, causing large losses of substance in many cases did not produce the required degree of purification. Neither is it possible by the method of purification disclosed in German Offenlegungsschrift No. 1,805,920 to eliminate all the troublesome by-products. Although according to this process, crude TCB is dissolved in aliphatic chlorinated hydrocarbons and precipitated by the addition of water the by-products cannot be removed.

It has now surprisingly been found that by-products can be eliminated completely from a solution of TCB in an aromatic (optionally chlorinated) hydrocarbon by washing the solution with hot water, followed by crystallization of the TCB from the aqueous solution.

Accordingly the present invention relates to a process for the production of very pure 2,2-bis-(4-hydroxy-3,5-dichlorophenyl)-propane (TCB) wherein a solution of the TCB, which is obtained by conventional chlorination methods of 2,2-bis-(4-hydroxyphenyl)-propane, in an aromatic hydrocarbon or halogenated aromatic hydrocarbon is treated at least once with water at a temperature in the range of from 60° to 100°C, the water-containing solution is cooled under simultaneous addition of an aliphatic halogenated hydrocarbon which is liquid at room temperature to cause precipitation of a crystalline adduct of TCB, water and the halogenated aliphatic hydrocarbon in a molar ratio of 2:3:1, from which a very pure TCB is obtained by drying or leaving said adduct standing on air.

The proportion of hydrolyzable chlorine detected by analytical methods is negligible so that the TCB obtained according to the inventive process is eminently suitable for the production of chlorinated polycarbonates by known methods.

Suitable solvents include mononuclear or polynuclear condensed aromatic hydrocarbons with 6 – 12 carbon atoms, which are liquid at room temperature and optionally substituted by chlorine or bromine, such as benzene, toluene or chlorobenzene. Usually a 10 to 65 % by weight solution, preferably a 50 to 60 % by weight solution of crude TCB in the aromatic solvent is treated at least once with 10 to 100 % by weight, based on the solution, of water. The purification effect is best when the solution provided with water is boiled under reflux.

Halogenated aliphatic hydrocarbons with 1 – 10 carbon atoms, preferably 1 – 6 carbon toms, for example methylene chloride, methyliodide, ethylbromide, 1,2-dichloroethylene, 1,2-dibromoethane and 1,4-dichlorobutane, are used as precipitants. From 10 to 100 % by weight, based on the organic phase, are required for precipitation.

EXAMPLE 1

3.5 kg of gaseous chlorine were introduced into a suspension of 2.28 kg of 2,2-bis-(4-hydroxyphenyl)-propane in 18.5 kg of methylene chloride over a period of 2 hours with stirring and cooling to 30°C, to yield 3.66 kg of TCB in the form of yellow-tinged crystals with a distinct chlorophenol odor as residue after the solvent and the excess chlorine has been distilled off.

This crude product which is also commercially available in similar quality has the following characteristics:

| | |
|---|---|
| Melting point | 131 – 132°C |
| Color of the melt (iodine tinting strength)* | iodine 50 |
| Hydrolysable chlorine | 740 ppm |
| Organic secondary products (according to gas chromatography) | 2.2% |
| Yield, based on pure TCB | 97.8 %. |
| *according to DIN 53 403 | |

Equal parts of the resulting crude TCB were purified in different ways and the products obtained were investigated for purity and yield. The results are set out in the following Table 1.

a. Comparison Example: 30.5 g of crude TCB were dissolved at 80°C in 20.3 g of chlorobenzene and the resulting solution was cooled with stirring over a period of 2 hours to a temperature of 20°C, beginning of crystallization 73°C. The crystals were filtered off, washed with 10 g of methylene chloride and subsequently dried. The mother liquor was freed from the solvent by vacuum distillation. The mother-liquor residue and pure crystals were investigated.

b. Comparison Example: 30.5 g of crude TCB were dissolved in chlorobenzene as in (a), the solution was boiled under reflux while stirring with 50 g of water for a period of 1 hour. The water layer was then separated off, another 50 g of water were added and the product was cooled as in (a); beginning of crystallization 75°C. Working up and investigation were also carried out as in (a).

c. 30.5 g of crude TCB were dissolved in chlorobenzene and treated with hot water as in (b) but the cooling step was accompanied by the dropwise addition of 20 g of methylene chloride: beginning of crystallization 65°C. Working up and investigation were carried out as described above.

d.–f. 3.5 g batches of crude TCB were purified in the different way as described in Tests (a)–(c), except that 30 g of benzene were used as solvent instead of 20.3 g of chlorobenzene, g. 30.5 g of crude TCB were purified in the same way as described in (c), except that 25 g of toluene were used as solvent instead of 20.3 g of chlorobenzene. In addition, 20 g of ethylene chloride were used instead of 20 g of methylene chloride for crystallization.

h. Comparison Example: 30.5 g of crude TCB were dissolved in 75 g of methylene chloride at 40°C and 75 g of water were added dropwise to the resulting solution with stirring over a period of 1 hour, crystallization began immediately (40°C). The product was then cooled to 20°C over a period of 1 hour and the resulting crystal sludge worked up and investigated in the same way as in (a).

i. Comparison Example: 30.5 g of crude TCB were dissolved at 70°C in 42 g of ethylene chloride, followed by the addition of 9 g of water. The product was then cooled to 20°C over a period of 2 hours and the crystal sludge worked up and investigated in the same way as described in (a).

EXAMPLE 2

Crude tetrachlorobisphenol A, obtained by chlorinating bisphenol in an inert solvent in the presence of $SO_2$ and nitrogen, has the following characteristics:

| | |
|---|---|
| Solidification point | 133.6°C |
| Color of the melt (iodine tinting strength) | iodine 1 |
| Hydrolysable chlorine | 275 ppm |
| Organic secondary products (according to gas chromatography) | 0.01 % |
| Yield, based on pure TCB | 100 %. |

This product was purified from different solvents in the same way as described in Example 1 (a)–(i). The results of the investigations are set out in Table II below.

Table I

| Test | Recrystallization of TCB-crude product (30.5 g, Example 1) in different solvents | | | | | | | | |
|---|---|---|---|---|---|---|---|---|---|
| | a) | b) | c) | d) | e) | f) | g) | h) | i) |
| Solvent | 20.3g ClB | 20.3g ClB | 20.3g ClB | 30 g Bz | 30g Bz | 30g Bz | 25g Tol. | 75g MC | 42g EC |
| Water treatment | — | 2×50g $H_2O$ | 2×50 g $H_2O$ | — | 2×50g $H_2O$ | 2×50g $H_2O$ | 2×50g $H_2O$ | 75g $H_2O$ | 9g $H_2O$ |
| Solvent addition | — | — | 20 g MC | — | — | 20 g MC | 20 g EC | — | — |
| Beginning of crystallization | 73°C | 75°C | 65°C | 65°C | 60°C | 65°C | 40°C | 70°C | |
| TCB-crystals | 26.8 g | 27.0 g | 29.2 g | 27.4 g | 26.9 g | 29.3 g | 29.1 g | 28.5 g | 28.1 g |
| Crystal form | very fine | very fine | coarse | very fine | fine | coarse | coarse | fine | coarse |
| Solidification point | 132.0° | 132.5° | 133.4° | 132.3° | 132.8° | 133.3° | 133.1° | 132.7° | 132.5° |
| Color of melt | iodine 30 | iodine 20 | iodine 5–6 | iodine 20 | iodine 10–15 | iodine 5 | iodine 6 | iodine 15 | iodine 15–20 |
| Hydrolyzable chlorine | 140 ppm | 20 ppm | <10 ppm | 180 ppm | 20 ppm | 15 ppm | 15 ppm | 115 ppm | 140 ppm |
| Organic secondary products | 0.37 % | 0.08 % | 0.02 % | 0.08 % | 0.04 % | 0.02 % | 0.03 % | 0.04 % | 0.05 % |
| Yield | 87.8 % | 88.5 % | 95.7 % | 89.8 % | 88.3 % | 96.1 % | 95.4 % | 93.4 % | 92.1 % |
| Mother liquor | 24 g | 24 g | 41 g | 35 g | 34 g | 48 g | 45 g | 74 g | 45 g |
| Residue of ML | 3.7 g | 3.5 g | 1.3 g | 3.1 g | 3.6 g | 1.15 g | 1.4 g | 2 g | 2.4 g |
| Organic secondary products in residue | 15.4 % | 18.6 % | 51.6 % | 21.0 % | 18.3 % | 58.2 % | 48.0 % | 33.0 % | 27.4 % |

Note:
ClB = chlorobenzene
Bz = benzene
Tol. = toluene
MC = methylene chloride
EC = ethylene chloride Table II

| Test | Recrystallization of TCB-crude product (30.5 g, Example 2) in different solvents | | | | | | | | |
|---|---|---|---|---|---|---|---|---|---|
| | a) | b) | c) | d) | e) | f) | g) | h) | i) |
| Solvent | 20.3g ClB | 20.3g ClB | 20.3g ClB | 30 g Bz | 30g Bz | 30g Bz | 25g Tol. | 75g MC | 42 g EC |
| Water treatment | — | 2×50g $H_2O$ | 2×50g $H_2O$ | — | 2×50g $H_2O$ | 2×50g $H_2O$ | 2×50g $H_2O$ | 75g $H_2O$ | 9 g $H_2O$ |
| Solvent addition | — | — | 20 g MC | — | — | 20g MC | 20g EC | — | — |
| Beginning of crystallization | 75°C | 77°C | 67°C | 67°C | 67°C | 63°C | 67°C | 40°C | 70°C |
| TCB-crystals | 27.2 g | 28.9 g | 29.6 g | 27.9 g | 27.5 g | 28.5 g | 29.5 g | 28.9 g | 28.5 g |
| Crystal form | very fine | very fine | coarse | fine | fine | coarse | coarse | fine | coarse |
| Solidification point | 133.6 | 133.7 | 133.8 | 133.6 | 133.6 | 133.8 | 133.8 | 133.8 | 133.7 |
| Color of melt | Hz 120 | Hz 90 | Hz 30 | Hz 120 | Hz 80 | Hz 50 | Hz 40 | Hz 80 | Hz 100 |
| Hydrolyzable chlorine | 80 ppm | 30 ppm | <10 ppm | 100 ppm | 30 ppm | <10 ppm | <10 ppm | 50 ppm | 80 ppm |
| Color of 10 % Na-salt solution | Hz 50 | Hz 40 | Hz 15 | Hz 60 | Hz 50 | Hz 20 | Hz 15 | Hz 30 | Hz 40 |
| Yield | 89.1 % | 94.6 % | 97.1 % | 91.5 % | 90.1 % | 96.9 % | 96.9 % | 94.6 % | 93.4 % |
| Mother liquor | 22 g | 23 g | 40 g | 34 g | 35 g | 50 g | 46 g | 74 g | 46 g |
| Residue of ML | 3.3 g | 1.6 g | 0.9 g | 2.6 g | 3.0 g | 1.0 g | 1.0 g | 1.6 g | 2.0 g |
| Organic secondary products in | | | | | | | | | |

Table II-continued

| Test | Recrystallization of TCB-crude product (30.5 g, Example 2) in different solvents | | | | | | | | |
|---|---|---|---|---|---|---|---|---|---|
| | a) | b) | c) | d) | e) | f) | g) | h) | i) |
| residue | 0.09 % | 0.19 % | 0.30% | 0.12 % | 0.10 % | 0.31 % | 0.30 % | 0.19 % | 0.15 % |

Note: ClB = chlorobenzene
Bz = benzene
Tol.= toluene
MC = methylene chloride
EC = ethylene chloride
Hz = Hazen tinting strength according to DIN 53 409

EXAMPLE 3

The tetrachlorobisphenols purified in accordance with Example 2 (a)–(i) were converted into polycarbonates by phosgenating their aqueous sodium salt solutions in suspension with methylene chloride by the interfacial condensation method, and their relative viscosities and melt tinting strengths compared with one another.

| Polycarbonates of the test products of Example 2 | | | |
|---|---|---|---|
| Tetrachloro-bisphenol purified in accordance with Example 2 | Properties of the polycarbonates | | |
| | $\eta$ rel. | Tinting strength | Assessment |
| a | 1.265 | 1.8 | dark-colored, HCl eliminated on melting |
| b | 1.270 | 1.5 | dark-colored, somewhat hazy |
| c | 1.285 | 0.5 | eminently suitable for use |
| d | 1.260 | 1.8 | dark-colored, HCl given off on melting |
| e | 1.265 | 1.2 | still too dark |
| f | 1.280 | 0.7 | eminently suitable for use |
| g | 1.285 | 0.6 | eminently suitable for use |
| h | 1.270 | 1.2 | HCl given off during thermoplastic processing, too dark |
| i | 1.275 | 1.3 | |

I claim:

1. A process for the production of very pure 2,2-bis-(4-hydroxy-3,5-dichlorophenyl)-propane (TCB) wherein a solution of the TCB, which is obtained by conventional chlorination methods of 2,2-bix-(4-hydroxyphenyl)-propane, in an aromatic hydrocarbon or halogenated aromatic hydrocarbon is washed with 10–100% of water, based on the weight of said solution, at a temperature of 60°–100°C, the resulting water layer is removed and to the remaining solution 10–100% of water is added, based on the weight of said solution, at a temperature of 60°–100°C, the resulting mixture of water and said solution is cooled with simultaneous addition of an aliphatic halogenated hydrocarbon which is liquid at room temperature to cause precipitation of a crystalline adduct of TCB, water, and the halogenated aliphatic hydrocarbon in a molar ratio of 2:3:1, from which pure TCB is obtained by drying.

2. The process of claim 1, wherein said aromatic hydrocarbon or halogenated aromatic hydrocarbon is a mononuclear or polynuclear condensed aromatic hydrocarbon of 6–12 carbon atoms.

3. The process of claim 2 wherein said hydrocarbon is benzene, toluene, or chlorobenzene.

4. The process of claim 1 wherein the initial solution contains 10 to 65% by weight of crude TCB.

5. The process of claim 1, wherein said aliphatic halogenated hydrocarbon contains 1–10 carbon atoms.

6. The process of claim 5, wherein said hydrocarbon is methylene chloride, methyliodide, ethylbromide, 1,2-dichloroethylene, 1,2-dibromoethane or 1,4-dichlorobutane.

* * * * *

UNITED STATES PATENT OFFICE
CERTIFICATE OF CORRECTION

PATENT NO. : 3,957,886
DATED : May 18, 1976
INVENTOR(S) : Karl-Heinrich Meyer

It is certified that error appears in the above-identified patent and that said Letters Patent are hereby corrected as shown below:

Column 2, line 57, "3.5" should read --- 30.5 ---.

Columns 3 and 4, Table 1, under Test e, fourth number down should be --- 65°C ---.

Columns 3 and 4, Table 1, under Test f, fourth number down should be --- 60°C ---.

Columns 3 and 4, Table 1, under Test g, fourth number down should be --- 65°C ---.

Columns 3 and 4, Table 1, under Test h, fourth line down should read --- 40°C ---.

Columns 3 and 4, Table 1, under Test i, fourth line down should read --- 70°C ---.

Signed and Sealed this

Twenty-fifth Day of April 1978

[SEAL]

Attest:

RUTH C. MASON
Attesting Officer

LUTRELLE F. PARKER
Acting Commissioner of Patents and Trademark